(12) United States Patent
McMurtry et al.

(10) Patent No.: US 8,510,929 B2
(45) Date of Patent: Aug. 20, 2013

(54) INDEXER

(75) Inventors: David Roberts McMurtry, Dursley (GB); Mark Stephen James Forman, Wotton-under-Edge (GB)

(73) Assignee: Renishaw PLC, Wotton-Under-Edge (GB)

( * ) Notice: Subject to any disclaimer, the term of this patent is extended or adjusted under 35 U.S.C. 154(b) by 331 days.

(21) Appl. No.: 12/919,692

(22) PCT Filed: Feb. 27, 2009

(86) PCT No.: PCT/GB2009/000540
§ 371 (c)(1),
(2), (4) Date: Aug. 26, 2010

(87) PCT Pub. No.: WO2009/106833
PCT Pub. Date: Sep. 3, 2009

(65) Prior Publication Data
US 2011/0000076 A1    Jan. 6, 2011

(30) Foreign Application Priority Data

Feb. 28, 2008   (GB) .................................. 0803666.7

(51) Int. Cl.
*B23Q 3/18*   (2006.01)
*B23Q 7/00*   (2006.01)

(52) U.S. Cl.
USPC ............................................. 29/559; 269/63

(58) Field of Classification Search
USPC .................... 29/559, 56.6, 721, 896.1, 281.1, 29/281.4, 281.5, 281.6; 269/63; 409/122, 409/88; 403/128
See application file for complete search history.

(56) References Cited

U.S. PATENT DOCUMENTS

| 4,651,405 | A | 3/1987 | McMurtry |
| 5,383,752 | A | 1/1995 | Rheinberger et al. |
| 5,678,967 | A | 10/1997 | Savoie |
| 5,733,126 | A | 3/1998 | Andersson et al. |
| 6,860,637 | B2 | 3/2005 | Hunter et al. |
| 6,905,293 | B1 | 6/2005 | Filser et al. |
| 7,228,641 | B2 | 6/2007 | Hunter et al. |

(Continued)

FOREIGN PATENT DOCUMENTS

| DE | 20 2005 003 439 U1 | 9/2005 |
| EP | 0 392 660 | 10/1990 |

(Continued)

OTHER PUBLICATIONS

Braddick, H.J.J., *Mechanical Design of Laboratory Apparatus*, 1960, pp. 11-30, Chapman & Hall, London.

(Continued)

*Primary Examiner* — John C Hong
(74) *Attorney, Agent, or Firm* — Oliff & Berridge, PLC

(57) ABSTRACT

This invention relates to an indexer for providing rotation of a part from a first index position to a second index position. The indexer comprises an indexer frame and a part for rotation. The indexer frame has at least one index feature, and the part has at least one index feature, wherein the at least one index feature on the indexer frame is co-operable with the at least one index feature on the part so as to provide two or more index positions of the part with respect to the indexer frame. In use the part locates with the indexer frame so as to form an axis about which the part is able to rotate relative to the indexer frame, the axis being kinematically located.

43 Claims, 14 Drawing Sheets

(56) References Cited

U.S. PATENT DOCUMENTS

| | | |
|---|---|---|
| 7,241,070 B2 | 7/2007 | McMurtry |
| 2005/0150125 A1 | 7/2005 | Hajdukiewicz et al. |
| 2007/0237595 A1 | 10/2007 | Steger |

FOREIGN PATENT DOCUMENTS

| | | |
|---|---|---|
| EP | 0 455 855 B1 | 11/1991 |
| EP | 0 674 969 A1 | 10/1995 |
| EP | 1 106 146 A1 | 6/2001 |
| EP | 1 243 842 A1 | 9/2002 |
| EP | 1 609 437 A1 | 12/2005 |
| GB | 2 277 593 A | 11/1994 |
| GB | 2 335 274 A | 9/1999 |
| WO | WO 03/062740 A1 | 7/2003 |
| WO | WO 2006/067630 A2 | 6/2006 |
| WO | WO 2009/106830 A1 | 9/2009 |

OTHER PUBLICATIONS

Great Britain Search Report issued in Great Britain Application No. 0803666.7 dated May 27, 2008.

International Search Report issued in International Application No. PCT/GB2009/000540 dated Oct. 5, 2009.

Written Opinion of the International Searching Authority issued in International Application No. PCT/GB2009/000540 dated Oct. 5, 2009.

May 29, 2012 Office Action issue in Chinese Patent Application No. 200980107080.8 (with translation).

Feb. 28, 2013 second Office Action issued in Chinese Patent Application No. 200980107080.8 (with English Translation).

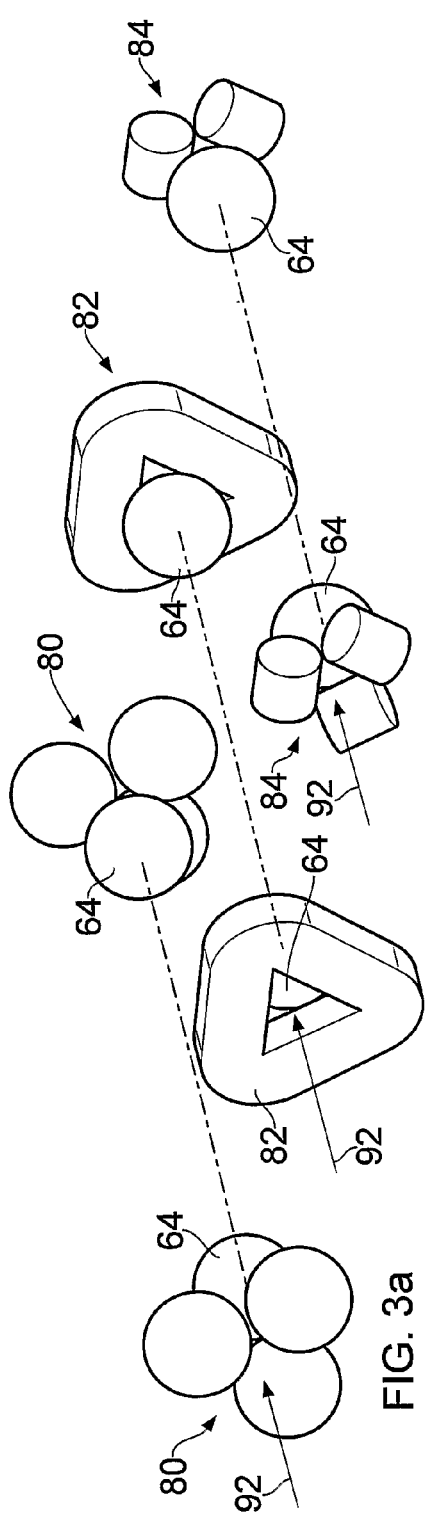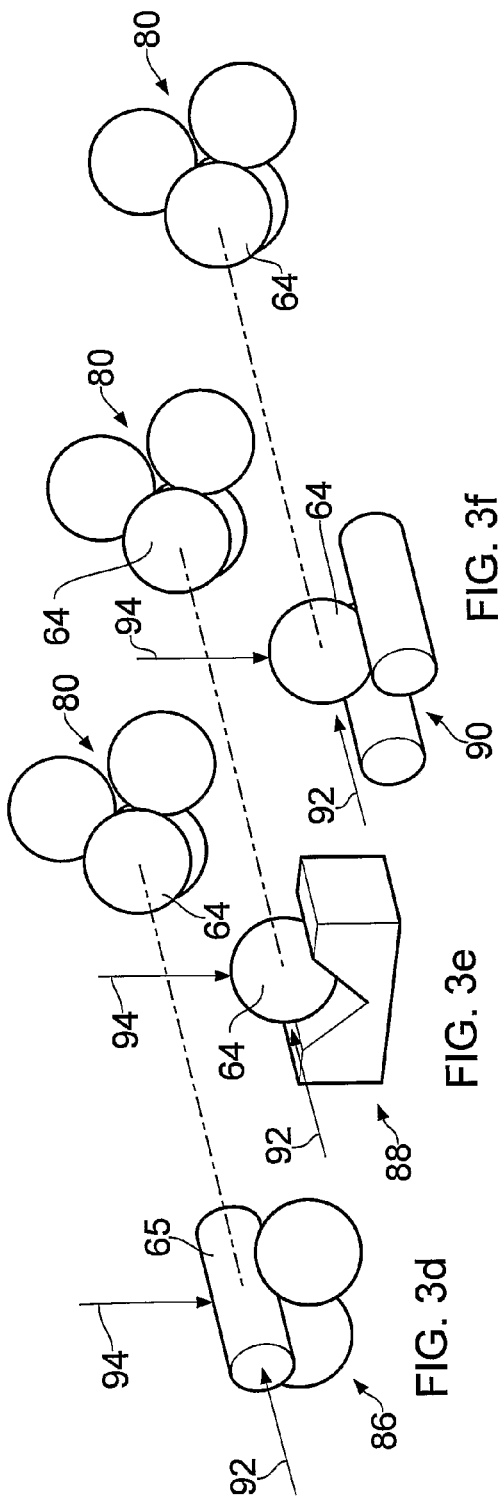

INDEXER

The present invention relates to an indexer and method for using said indexer to position a part. In particular, but not exclusively, the invention relates to an indexer for use in dental apparatus.

In the field of dentistry it is desirable to be able to scan the form of a three-dimensional object and reproduce the form, for example by milling it from a billet. In order to scan an object a probe must be moved relative to the object, or vice versa; the same is true for milling where relative movement is required between a tool and a billet.

Scanning of three-dimensional objects may be achieved by providing a probe which has three-dimensional movement such that the probe can access the whole surface of the stationary sample; however this requires a relatively large working space and so is unsuitable for applications where there are size limitations. The probe may be a contact probe, such as a touch trigger or scanning probe, or a non-contact probe such as an optical, capacitance or inductive probe.

An alternative method for scanning three-dimensional objects, which reduces the working space required, is disclosed in Renishaw's European patent application EP1468242. EP1468242 describes how the sample is held in position by a reorientatable holder which is adapted on at least two sides to be repeatably mounted on a base. The relationship between the different orientations of the sample when different surfaces of the reorientatable sample holder are received on the base is known. The sample is scanned in one orientation, reorientated, and scanned in the new orientation. The data from the scans of the sample in each orientation are then matched together to obtain the data for a scan of the whole sample. In order to match together the scans a reference object must be scanned at each orientation of the sample. This is a time consuming step in the scanning process. As an alternative to scanning a reference sample, computer processing and software can be used to match up overlapping scans, this can also be time consuming.

A further disadvantage of this method is that the part has to be manually reoriented. Thus the process requires human intervention at regular intervals throughout the scan.

The invention relates to an indexer for providing rotation of a first part relative to a second part between at least first and second indexed positions in which the axis of rotation between the at least first and second parts is kinematically located.

According to a first aspect of the present invention an indexer for providing rotation of a part from a first index position to a second index position comprises:

an indexer frame and a part for rotation, said indexer frame having at least one index feature, and said part having at least one index feature, wherein the at least one index feature on the indexer frame is co-operable with the at least one index feature on the part so as to provide two or more index positions of the part with respect to the indexer frame;

wherein in use the part locates with the indexer frame so as to form an axis about which the part is able to rotate relative to the indexer frame, said axis being kinematically located.

The kinematically located axis has the advantage that the position of the axis defined relative to the indexer frame is highly repeatable. Consequently, as the part rotates about the axis, each index position can be highly repeatable. The use of a kinematically located axis guarantees repeatability of the axis without relying on precisely machined parts, this makes the indexer cheap and easy to construct.

Additionally, as the relative position of the part at each index position is accurately known after a single calibration process, recalibration of the position of the part relative to the probe at each orientation of the part is not required. If, for example, a scanning procedure is being carried out on the part there is no need for a reference object to be scanned at each orientation of the part. The scans of the part at each index position can be matched together without the need for a reference object. This saves time in the process of scanning or machining a part.

As will be understood, and as for instance described in H. J. J. Braddick, "Mechanical Design of Laboratory Apparatus", Chapman & Hall, London, 1960, pages 11 to 30, kinematic design involves constraining the degrees of freedom of motion of a body or feature using the minimum number of constraints and in particular involves avoiding over constraining. In this case the feature being constrained is an axis of rotation. As will be understood, over constraining can occur when the points of contact between bodies enable the feature's location to rest in more than one position. Accordingly, the feature's location is not repeatable as it is not known at which of the at least two positions the feature will be located when the bodies are assembled. With an axis, such over constraining could cause the axis to be not truly repeatable, i.e. it could be positioned at one of at least two positions depending on how the part and indexer frame are assembled. It could also mean that the axis is susceptible to wobbling during rotation. This can be avoided by ensuring that only one rest position is provided. If more than one rest position is provided, then a bias can be provided to ensure that the bodies are always forced into one of the many rest positions to ensure kinematic design considerations are met.

Accordingly, preferably the features on the indexer frame and the part that cooperate to facilitate rotation between the indexer frame and the part are configured to between them define an axis of rotation that is kinematically located, i.e. a kinematic axis.

With the kinematic axis of the invention, the features defining the axis are the same at each of the indexed positions. Only the index features which constrain rotation about the axis change between each of the indexed positions.

Nevertheless, as will be understood, at least one of the index features on the part or indexer frame which are used to constrain rotation about the axis can be the same at each indexed position.

The axis can be defined by at least two spaced apart engagement locations between the indexer frame and the part. Preferably, cooperating features on the part and indexer frame at one of the engagement locations are configured to constrain the axis in at least one degree of freedom, and cooperating features on the part and indexer frame at the at least one other engagement location are configured to constrain the axis in at least one other degree of freedom. Preferably, cooperating features at the at least one other engagement location are configured to constrain the axis in the remaining degrees of freedom (apart from rotation about the axis). In particular, a first one of the engagement locations can be configured to constrain a point of the axis in at least one translational degree of freedom, preferably at least two mutually perpendicular translational degrees of freedom, especially preferably at least three mutually perpendicular translational degrees of freedom. At least one other engagement location can be configured to constrain movement of the axis in at least one rotational degrees of freedom, preferably at least two rotational degrees of freedom about the first engagement location.

The at least one other engagement location can be compliant in one of the degrees of freedom that the first one of the engagement locations provides constraint. Preferably, the at least one other engagement location is compliant in a dimension parallel to the axis. Such compliance can help avoid over constraining the axis. For instance, the points of contact between the cooperating features at each engagement location can define a contact plane. Preferably, one the contact plane of one of the engagement locations is fixed relative to the part and indexer frame and the contact plane of the other engagement location is resiliently displaceable. Preferably the contact plane is defined by not more than three points of contact between the cooperating features of the part and indexer frame at a given engagement location.

In order to constrain five degrees of freedom the minimum number of constraints is five. This could be provided for example by five rigid contacts. However, as will be understood, and as explained in more detail below, more rigid contacts could be used without over constraining the axis.

Conveniently the indexer frame can comprise two opposing frame ends spaced apart by a frame body. This provides a structure such that the axis can be fixed at two spaced apart points.

Preferably one frame end is biased towards the other end frame by a bias mechanism. More preferably the bias mechanism comprises a spring. Alternatively, the bias mechanism may be for example magnetic, or a hydraulic cylinder. The bias mechanism provides a force which positively locates the part in the indexer frame. An advantage of compliance in one frame end is that it enables the axis to remain repeatable even if there is some wear to the parts and can therefore reduce the need for tight tolerances on the parts.

Preferably, the said location between the part and the indexer frame is facilitated by cooperation between corresponding recesses and protrusions provided on the part and indexer frame. For instance, at least a first protrusion on one of the indexer frame and part can be provided for cooperation with at least a first corresponding recess on the other of the part and indexer frame at a first location. Likewise, at least a second protrusion on one of the indexer frame and part can be provided for cooperation with at least a second corresponding recess on the other of the part and indexer frame at a second location. The axis can be kinematically located by a recess on the indexer frame cooperating with a protrusion on the part at two locations, or vice versa by a protrusion on the indexer frame cooperating with a recess on the part at two locations. Preferably one cooperating recess and protrusion couple are separated from the other cooperating recess and protrusion couple, i.e. the two locations are separated.

Advantageously a recesses may comprise a triangular recess. Advantageously a protrusions can comprise a ball. Triangular recesses can be effective at constraining in three degrees of freedom due to the three sides forming three points of contact with the protrusion. Balls can be effective protrusions due to their uniform sphericity.

Alternatively the recesses may comprise, for example, other trihedral recesses such as a cluster of three balls or three rollers, or a combination of a trihedral recess at one end of the axis and a dihedral recess at the other end of the axis, such as a vee-groove, two balls together, or two rollers together. As will be understood, when using a combination of a trihedral recess and a dihedral recess an extra force locating the protrusion into the dihedral recess could be required to ensure a firm kinematic location. This might be provided by a bias device, such as a spring for instance.

The protrusions may alternatively comprise, for example, rollers.

Preferably, the indexer frame is configured to have a first position for locating the part and a second position beyond which the part is released. This has an advantage that the part may be removed from the indexer frame and replaced in the indexer frame repeatably, such that the position of the axis about which the part rotates is known. The part can be removed and replaced sufficiently repeatably that recalibration of the position of the part relative to the probe is not required. Being able to remove the part from the indexer allows it to be inspected or worked on away from the indexer. The user may wish to swap the original part for a different part, the axis of rotation of which will also be known. This is particularly advantageous in the dental field as the user may wish to remove a billet and its holder once it has been machined and replace it with a new, unmachined billet and billet holder to be machined whilst the first billet is being inspected.

Advantageously, movement between said first and second position may be provided for by the moveable frame end. More advantageously, the moveable frame end may be sprung with respect to the indexer frame so as to allow movement between said first and second positions.

Conveniently, the indexer may be adapted for mounting on dental apparatus. Such dental apparatus includes, for example, a dental milling machine and a dental scanning machine. The indexer may be particularly useful in the dental industry due to the small and complex three-dimensional shape of dental parts, and also due to size constraints on the dental apparatus itself. The indexer may also be used in the machining of small three-dimensional parts in any industry, or in scanning any small, three-dimensional parts, in any industry. The indexer is particularly useful in the ceramic industry.

The part may comprise a workpiece. For instance, the part could comprise a workpiece to be inspected by a workpiece inspection tool. Optionally, the part could comprise a workpiece to be worked on by a tool. For instance, the workpiece could be a billet. The part preferably comprises a workpiece holder. For instance, the part could comprise a billet holder. For example, the part may comprise a billet for machining dental parts from, a ceramic billet for machining any small three-dimensional part from, a dental prosthesis, or any other small three-dimensional part. Alternatively the part may be adapted to provide a platform for holding a sample for scanning or for machining. The part may be a 'set-up' block as described hereinbelow.

One of the indexer frame and part can have two or more index features and the other of the indexer frame and part can have one or more index features, thus providing two or more index positions of the part with respect to the frame. Conveniently two index positions of the part with respect to the indexer frame may be provided. These two positions may be provided by two index features on the part, both co-operable with one index feature on the indexer frame, or vice versa. For procedures such as milling and scanning dental prosthesis it is common to require access to the top and under-side of the billet from which the prosthesis is machined or of the prosthesis itself; two index positions enables this to be achieved.

Preferably the index positions are kinematically located. More preferably, the kinematic location of the index positions is achieved by cooperating index features provided on the part and the indexer frame.

When the part is kinematically located in any of its index positions the motion of the part is constrained in six degrees of freedom using the minimum number of constraints (six constraints is the minimum number required to constrain six degrees of freedom). Movement of the part is constrained in five degrees of freedom by the kinematically located axis as discussed previously. The only movement available to the part when mounted in the indexer frame is rotation about the axis. To achieve the index positions the part can be further constrained, preventing rotation about the axis. The advantage of kinematically locating the part relative to the indexer frame is that the position of the part in one index position is known relative to the position of the part in another index position. This enables scanning or machining carried out with the part at different index positions to be easily coordinated and matched together without the need for, for example, scanning reference objects and further calibration. The part is consequently located accurately and precisely without great expense in making precise and accurate components of the indexer and frame.

Preferably the index features providing each kinematically located index position comprise at least one protrusion on the part and at least one corresponding recess on the indexer frame. Alternatively the index features may comprise at least one protrusion on the indexer frame and at least one recess on the part. Preferably, one of the indexer frame and part have a plurality of index features defining a plurality of index positions. The other of the indexer frame and part can have at least one index feature for cooperating with at least one of the plurality of the plurality of index features on the indexer frame to locate the indexer frame and part at an index position. The number of index features on the indexer frame and the part need not be the same. For instance, one of indexer frame and part could have just one index feature for cooperating with each of the index features provided on the other of the part and indexer frame. Preferably, the position of at least one of the index features on one of the part and indexer frame is selectively adjustable. Optionally, the position of the index features on the part and indexer frame that has a greater number of index features are selectively adjustable. Preferably, the index features on the other of the part and indexer frame are fixed.

At least two protrusions can be provided on the part for cooperation with at least one recess on the indexer frame. Preferably at least two recesses are provided on the indexer frame for cooperation with at least one protrusion on the part. More preferably, one protrusion is provided on the part It has been found that it can be easier to accurately align the recesses on the indexer frame, for example to provide index positions rotationally spaced apart by 180°, than to accurately align protrusions on the part. This is particularly the case in embodiments in which the protrusions are machined into the solid block from which the part is made whereas the recesses are provided on an arm, the position of which can be adjusted relative to the main body of the frame in order to align the recesses. In this case an accurately machined 'set-up' part may be used in order to align the recesses; thus only one accurately machined 'set-up' part is required in order to configure many indexer frames, each frame providing accurately spaced recesses to provide accurate index positions in cooperation with a single protrusion on a part.

The 'set-up' block may locate in the indexer frame in place of the part. The 'set-up' block may thus locate with the indexer frame so as to form an axis about which the 'set-up' block is able to rotate relative to the frame, said axis being kinematically located. Preferably the axis is kinematically located by a recess on the indexer frame cooperating with a protrusion on the 'set-up' block at two locations, or vice versa by a protrusion on the indexer frame cooperating with a recess on the 'set-up' block at two locations, as described above with reference to the part and the indexer frame.

Advantageously the 'set-up' block is provided with index features for cooperation with index features on the indexer frame. Specifically the index features on the 'set-up' block may be accurately positioned such that the index features on the indexer frame may be aligned with the index features on the 'set-up' block. Conveniently the index features on the 'set-up' block may comprise two protrusions accurately separated by 180°. It will be understood that any number of index features, accurately separated from one another, may be provided. The index features may be machined as part of the 'set-up' block, or machined separately and attached to the 'set-up' block.

Advantageously, the protrusion can be a tapered pin. Advantageously the recess can be a slot with at least two straight, parallel and substantially opposing sides. An advantage of using a tapered pin is that the angle of contact with the recess is always known. This angle can be required to calculate the amount of force that can be applied without the pin coming out of the slot (this may be important during milling or contact scanning as external forces may be applied to the part).

An advantage of using a slot with at least two straight sides positioned radially out from the rotation axis is that the straight sides prevent the part from rotating about the axis. One straight side prevents rotation in a clockwise direction, and the other straight side prevents rotation in an anticlockwise direction; thus together they prevent rotation of the part about the axis, restricting one degree of freedom of the part. The width of the slot gives some tolerance to the relative positioning of the index features such that the parts of the indexer frame can be put together without great accuracy.

Alternatively the index features may, for example, be a protrusion cooperating with a stop, and a magnet to hold the protrusion against the stop, or a straight edged pin cooperating with a tapered hole.

Preferably, any index features on one of the part and the indexer frame are moveable relative to any index features on the other of the part and the indexer frame between an engaging and a disengaging position. This enables disengagement of the index feature of the part from the index feature of the indexer frame to allow rotation of the part about the axis from a first index position to a second index position. It also enables re-engagement of the index feature of the part with the index feature of the indexer frame to kinematically locate the part at an index position. The index feature may be moveable in any direction, as long as it is stiff in the direction of rotation of the part about the kinematically located axis, such that it prevents rotation in said direction.

Preferably any moveable index feature is provided on an arm sprung with respect to the indexer frame.

The indexer may be provided with a calibration feature, for example a ball on the end of a stylus. It will be understood that any other feature that is able to provide a repeatable reference point may be used in the place of the ball on the end of a stylus. When the indexer is in use, for example in dental apparatus, a measurement probe may be provided on the dental apparatus such that the measurement probe can determine the position of the calibration feature located on the indexer. The calibration feature may be located relative to the position of the part of the indexer such that the position of the part can be obtained by contacting the calibration feature with a measurement probe. Where the dental apparatus is for example a dental milling machine or a dental measuring machine, preferably a measurement probe is used to contact the calibration feature after each time the power to the machine is switched on, before any measuring or machining activity is carried out.

According to a second aspect of the present invention a part for use with an indexer frame comprises:

at least one index feature, which in use is co-operable with at least one corresponding index feature on an indexer frame to provide at least two index positions;

axis locating means which in use locates with an indexer frame so as to form an axis about which the part is able to rotate relative to the frame.

Preferably, the at least one index feature is a tapered pin. More preferably, the locating means are balls.

According to a third aspect of the present invention an indexer frame for use with a part comprises:

at least one index feature, which in use is co-operable with at least one corresponding index feature on a part to provide at least two index positions;

axis locating means which in use locates with a part so as to form an axis about which the part is able to rotate relative to the frame.

According to a fourth aspect of the present invention a method for indexing a part located in an indexer frame and rotated about a kinematic axis between a first index position relative to the indexer frame and a second index position relative to the indexer frame, comprises:

disengaging a first set of cooperating index features on the indexer frame and the part, said index features defining a first index position of the part relative to the frame;

rotating the part relative to the frame about the kinematic axis;

engaging a second set of cooperating index features on the indexer frame and the part, said index features defining a second index position of the part relative to the frame.

Preferably the index feature on one of the part and the frame is the same index feature for the first and second sets of cooperating index features.

The first set of cooperating index features may comprise a first index feature on the indexer frame and a first index feature on the part; and the second set of cooperating index features may comprise the first index feature on the indexer frame and a second index feature on the part. Alternatively, the first set of cooperating index features may comprise a first index feature on the indexer frame and a first index feature on the part; and the second set of cooperating index features may comprise a second index feature on the indexer frame and the first index feature on the part.

Advantageously the index features comprise a tapered pin and a slot.

Conveniently, an index feature on the indexer frame can be provided on an arm sprung with respect an indexer frame body. More conveniently the index feature provided on the arm can be disengaged from any index features on the part by movement of the arm away from its biased position. Preferably the arm is moved away from its biased position by interaction with a feature on the machine body. For example the feature on the machine body may be a magnet, or a hook for engaging the arm.

Preferred embodiments of the invention will now be described, by way of example only, with reference to the following drawings, wherein:

FIGS. 3a to 3f show alternative arrangements for achieving a kinematic axis about which a billet holder may rotate in an indexer frame;

Figure 1A:
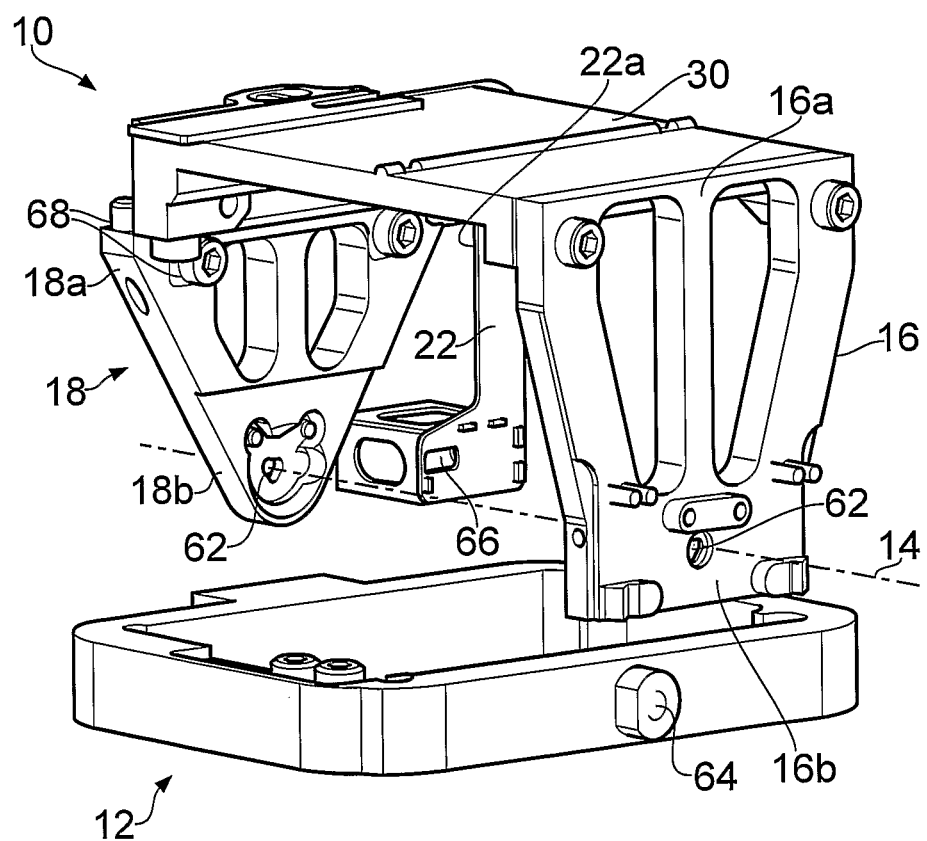
FIG. 1a is an isometric drawing of an indexer frame and a billet holder.

Referring to the figures, FIG. 1a shows an isometric drawing of an indexer frame 10 and a part 12, which in the described embodiment is a billet holder 12. In the present embodiment the billet holder 12 is a rectangular shaped frame for holding a billet (not shown). The indexer frame 10 comprises a fixed end member 16, a sprung end member 18, an indexer frame body 30 and a locking arm 22. The two end members 16, 18 are connected at their proximal ends 16a, 18a to opposing sides of the indexer frame body 30. These end members 16, 18 extend substantially perpendicularly away from the indexer frame body 30.

Figure 2:
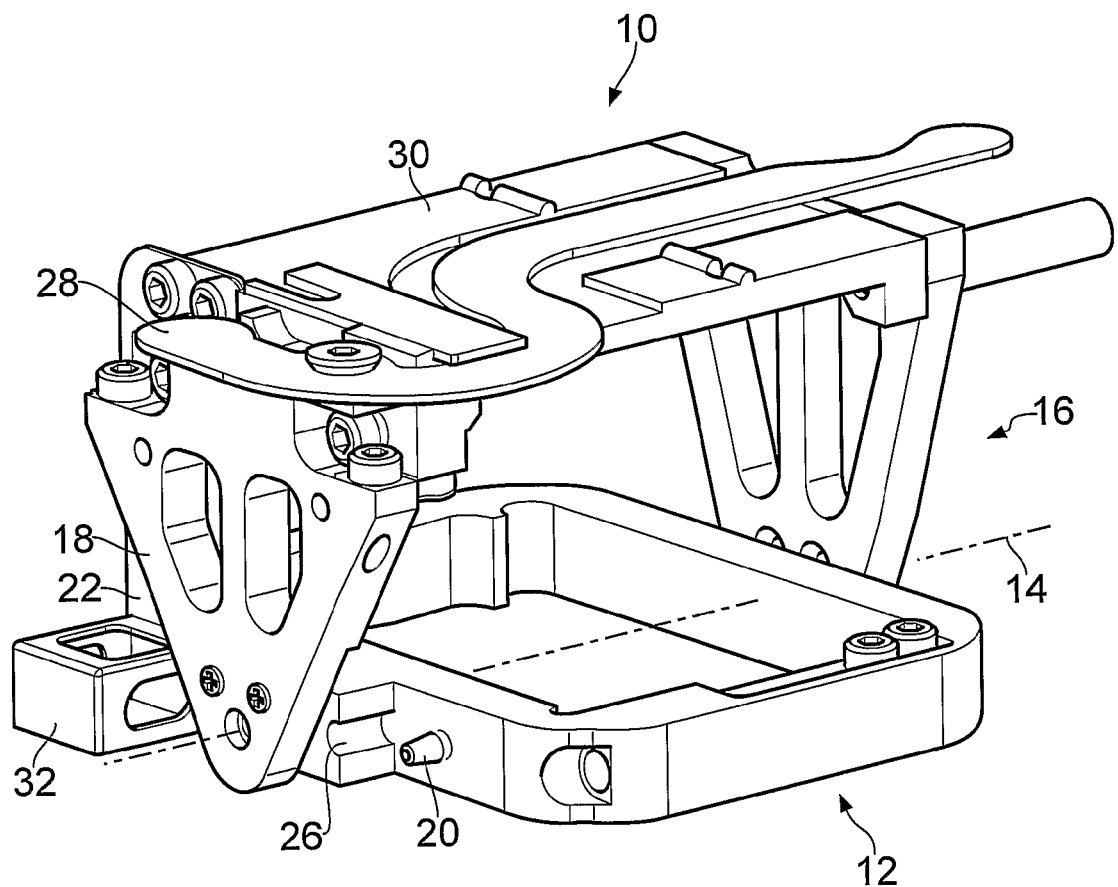
FIG. 2 shows an isometric drawing of the indexer frame of FIG. 1a holding a billet holder.

The sprung end member 18 is moveably connected to the indexer frame body 30 by two pairs of crossed planar springs 68 (only one pair is shown). These springs 68 bias the sprung end member 18 towards the fixed end member 16 and into a position substantially perpendicular to the indexer frame body 30, as mentioned previously. Movement of the sprung end member 18 against the bias, away from the fixed end member 16, is effected by a lever system 28 (as shown in FIG. 2). The fixed end member 16 is fixedly connected at its proximal end to the indexer frame body 30. At their distal ends 16b, 18b the end members 16, 18 each have a triangular recess 62 which in use each receive a ball 64 (only one is shown) on the billet holder 12.

In order for the billet holder 12 to be positioned in the indexer frame 10 the sprung end member 18 is moved against the bias of crossed planar springs 68 (shown in more detail in FIG. 4a) to increase the distance between the recesses 62. Once the balls 64 are located in the recesses 62, the sprung end member 18 is released back into its biased position, securely holding the billet holder 12 in place. Each ball 64 has three points of contact with each triangular recess 62.

To release the billet holder 12 from the indexer frame 10 the sprung end member 18 is moved against the bias of the springs 68 again. The billet holder 12 is kinematically located in the indexer frame 10, and the position of the billet holder 12 in the indexer frame 10 is repeatable to an accuracy of at least approximately 1 to 2 microns.

A locking arm 22 is located adjacent the sprung end member 18. The locking arm is connected at its proximal end 22a to the indexer frame body 30 and extends substantially perpendicularly away from the indexer frame body 30. At its distal end 22b the locking arm 22 is provided with an index feature, in this case a slot 66, for cooperation with index features 20 provided on the billet holder 12 (as shown in FIG. 2). The width of the slot gives some flexibility to the manufacture of the indexer. In particular, it enables the locking arm to be mounted onto the indexer frame within a range of positions whilst still enabling the slot to engage with the index features 20 of the billet holder 12.

The locking arm 22 is constructed of thin flexible metal such that the distal end 22b of the locking arm 22 is moveable relative to the indexer frame body 30. This flexibility allows the locking arm 22 to engage and disengage index features 20 provided on the billet holder 12. The billet holder 12 is provided with two index features 20 such that two indexed positions can be achieved, one by cooperation of the first index feature with the locking arm 22, and another by cooperation of the second index feature with the locking arm 22.

Figure 1B:
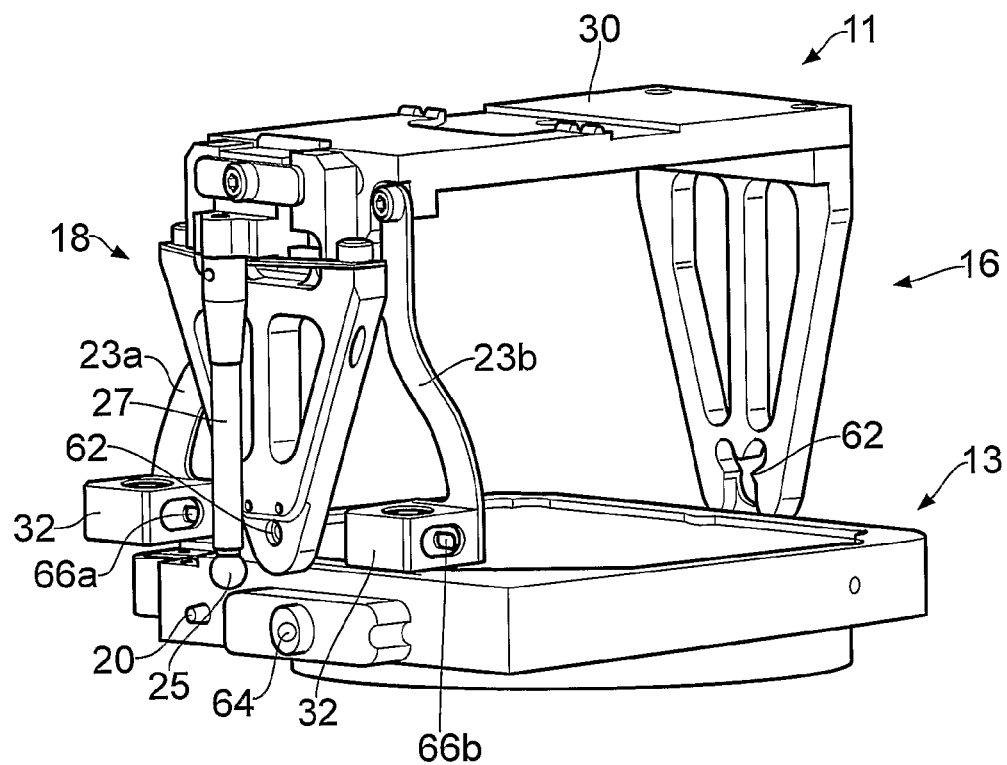
FIG. 1b is an isometric drawing of an alternative indexer frame and billet holder.

FIG. 1b shows an isometric drawing of an alternative indexer frame 11 and billet holder 13. The alternative indexer frame 11 is provided with two locking arms 23a, 23b located adjacent the sprung end member 18 of the frame. The sprung end member 18 is moveably connected to the indexer frame body 30 by two coil springs and a ball and roller arrangement, instead of two pairs of crossed planar springs as described with reference to FIG. 1a and FIG. 4a. The balls and roller arrangement is described in more detail with reference to FIG. 4b below. The billet holder 13 shown in FIG. 1b is provided with only one index feature 20. This index feature can cooperate with each of the two locking arms 23a, 23b, thus providing two indexed positions of the billet holder 13 relative to the indexer frame 11.

The indexer frame 11 shown in FIG. 1b additionally comprises a calibration feature comprising a ball 25 on a stylus 27. In use the indexer frame 11, holding the billet holder 13, is mounted to a machine structure which is moveable relative to the body of a machine. The ball 25 is provided such that information about the position of the indexer frame, and thus of the billet to be machined, may be obtained before any machining operation is carried out. For example, a touch trigger probe provided on the machine may be touched onto the ball 25. The position of the ball 25 relative to the position of the billet holder 13, and thus the billet held within the billet holder 13, is known such that when the touch trigger probe touches on the ball 25 the position of the billet within the machine volume is known. It will be understood that the calibration feature may be provided on any embodiment of the indexer.

Figure 1C:
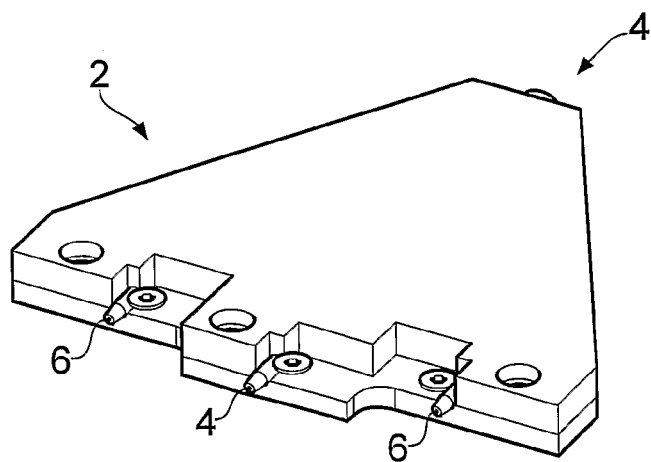
FIG. 1c shows an isometric drawing of a 'set-up' block for configuring the position of the index features of the indexer frame.

FIG. 1c shows an isometric drawing of a 'set-up' block 2 for configuring the position of the recesses 66a,b of the locking arms 23a,b of the indexer frame 11 as shown in FIG. 1b. The locating pins 4, positioned on either side of the block 2, locate into the triangular recesses 62 of the indexer frame in place of the billet holder. Two further index feature pins 6 are provided on one side of the 'set-up' block. These index feature pins 6 are accurately separated from each other by 180°; the index feature pins 6 are spaced apart astride the locating pin 4. Once positioned in the indexer frame 11 the block 2 is used to align the position of the recesses 66a,b with the index feature pins 6. This ensures that the recesses 66a,b are accurately separated by 180° and thus that when the indexer frame is in use with the billet holder the two indexed positions of the billet holder are accurately separated by 180°. By ensuring that the two indexed positions of the billet holder are accurately separated by 180°, any machining or scanning of the billet in the billet holder in its two indexed positions can be matched together without the need for a reference object. This saves time in the process of scanning or machining a part.

FIG. 2 shows an isometric drawing of an indexer frame 10 holding a billet holder 12. The balls 64 on the billet holder are received in the triangular recesses 62 in the indexer frame 10, such that an axis of rotation 14 is created about which the billet holder 12 may rotate relative to the indexer frame 10. As mentioned above, the billet holder 12 is constrained with respect to the indexer frame 10 in five degrees of freedom. The only degree of freedom available to the billet holder is rotation about the axis 14.

For any body all six degrees of freedom may be constrained, in which case the body is fixed in position and orientation (a 'kinematic mount'). Alternatively the body may be only partially constrained, for instance with five degrees of freedom constrained, in which case the body will be free to, e.g., rotate about an axis (a 'kinematic axis').

The axis 14 about which the billet holder 12 is able to rotate is kinematically located. The kinematically located axis 14 is constrained in five degrees of freedom, achieved in this example by five rigid points of contact. The only degree of freedom available to the part is rotation about the axis. As will be understood, the degrees of freedom of motion of the billet holder are achieved using the minimum number of constraints.

At the fixed end 16 the three points of contact with the triangular recess 62 provide three rigid contacts, whereas at the sprung end member the three points of contact with the triangular recess 62 only provide two rigid points of contact. This is due to the recess having one degree of freedom itself. Movement of the billet holder 12 with respect to the indexer frame 10 is thus constrained in five degrees of freedom by five rigid contacts, the minimum number of contacts required to achieve constraint in five degrees of freedom.

FIGS. 3a to 3f show alternative arrangements for achieving a kinematic axis about which the billet holder may rotate in the indexer frame. The five rigid contacts required may be achieved, as shown in FIG. 3a, by the balls 64 on the billet holder each contacting a cluster of three balls 80. FIG. 3b shows how the five rigid contacts required may be achieved by the balls 64 on the billet holder each contacting a triangular recess 82 (as previously described with reference to FIG. 1a). FIG. 3c shows how the five rigid contacts required may be achieved by the balls 64 on the billet holder each contacting an arrangement of three rollers 84. In the embodiments shown in FIGS. 3a to 3c the contact at one end of the axis is sprung (in the direction of the arrows 92) such that the three physical points of contact at that end have a degree of freedom and thus only contribute two rigid points of contact.

Alternatively, FIG. 3d shows a roller 65 at one end of the billet holder in place of a ball 64 shown in FIGS. 3a, b, c, e, and f. FIG. 3d shows how the five rigid contacts may be achieved by a ball 64 on the billet holder contacting three balls 80 (or alternatives) and a roller 65 on the billet holder contacting two balls 86. FIG. 3e shows how the five rigid contacts may be achieved by one ball 64 on the billet holder contacting three balls 80 (or alternatives) and the other ball 64 on the billet holder contacting a vee-groove 88. FIG. 3f shows how the five rigid contacts may be achieved by one ball 64 on the billet holder contacting three balls 80 (or alternatives) and the other ball 64 on the billet holder contacting two rollers 90. In each of FIGS. 3d to 3f a total of five physical contacts are made between the billet holder and the indexer frame. At the end of the billet holder where only two physical contacts are made the end must be sprung as before (in the direction of the arrows 92), and must have an additional force positively locating the ball against its two points of contact (in the direction of the arrows 94). This arrangement results in five rigid points of contact and thus results in a kinematically located axis.

Referring back to FIG. 2 the billet holder 12 is provided with two index features 20 (only one is shown) for cooperating with the index feature on the locking arm 22 of the indexer frame 10, in order to provide two index positions. In this case, the index features on the billet holder 12 are tapered pins 20. The tapered pins 20 are located on the side of the billet holder 12 facing the locking arm 22 of the indexer frame 10.

The billet holder 12 has a first indexed position, lying substantially parallel to the indexer frame body 30 of the indexer frame 10. In this position one tapered pin on the billet holder engages with the slot on the locking arm 22. A second indexed position is achieved by rotating the billet holder 12 relative to the indexer frame 10, through 180° about axis 14. In this position the other tapered pin 20 engages with the slot 66 on the locking arm 22. Both indexed positions are kinematically located due to five degrees of freedom being constrained by the location of the axis and the sixth degree of freedom being constrained by the tapered pin in the slot. Movement of the part relative to the indexer frame is constrained using the minimum number of rigid contacts. FIG. 1b describes an alternative indexer frame having two locking arms 23a,b and an alternative billet holder having just one tapered pin 20. Two index positions are provided again, and achieved again by rotating the billet holder 13 relative to the indexer frame 11 through 180°. This time however, the single tapered pin 20 cooperates with the first locking arm 23a to provide a first indexed position, and the second locking arm 23b to provide a second indexed position.

Figure 4A:
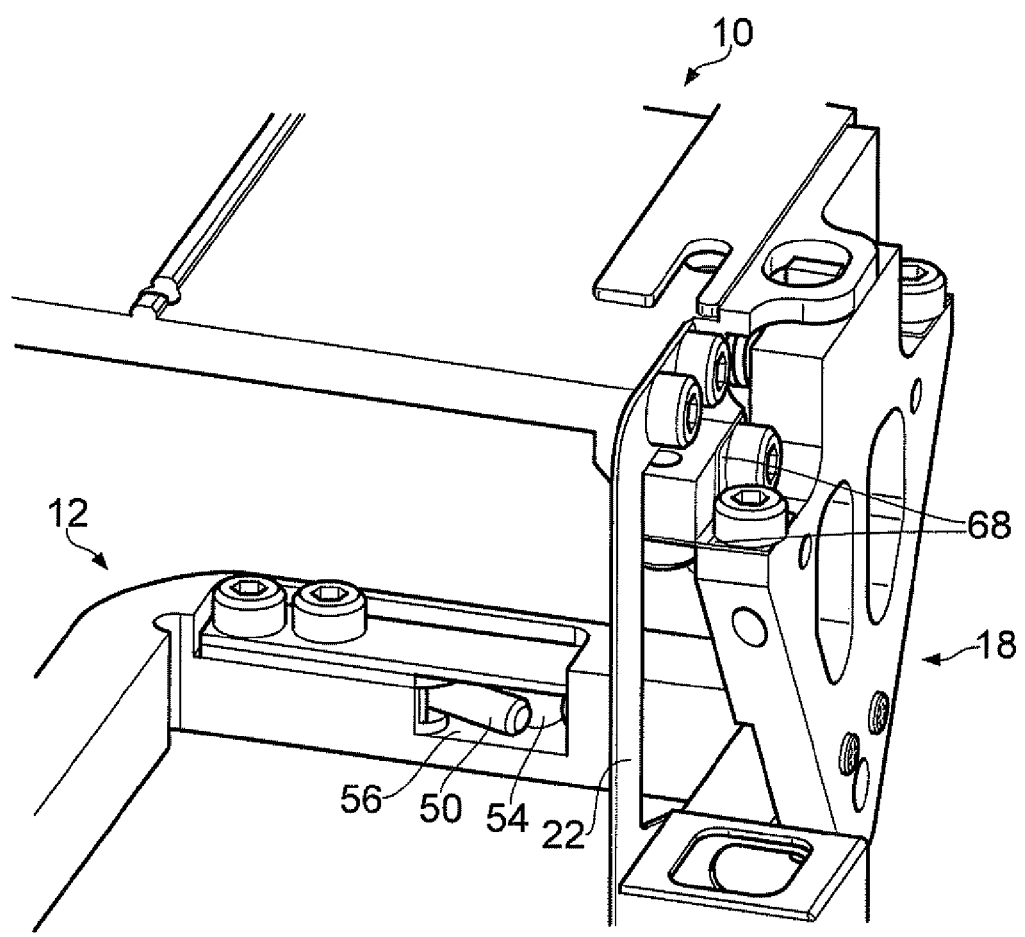
FIG. 4a shows a detailed view of the sprung end of the indexer frame shown in FIG. 1a, and the billet holding mechanism of a billet holder.

FIG. 4a shows in more detail the crossed planar springs 68 which bias the sprung end member 18 into position and enable the sprung end member 18 to move relative to the indexer frame body 30. Crossed planar springs 68 are used such that only one degree of freedom is available to the triangular recess 62; they prevent movement of the sprung end member 18 relative to the indexer frame body 30 in any direction other than towards and away from the fixed end member 16. Consequently the triangular recess 62, although providing three physical points of contact with the ball 64, only constrains two degrees of freedom of the ball 64. Movement of the sprung end member 18 against the bias, away from the fixed end member 16, is effected by a lever system 28. It will be understood that this lever system is not essential and that movement against the bias can be effected by other means, such as by manually forcing the sprung end member against the bias.

Figure 4B:
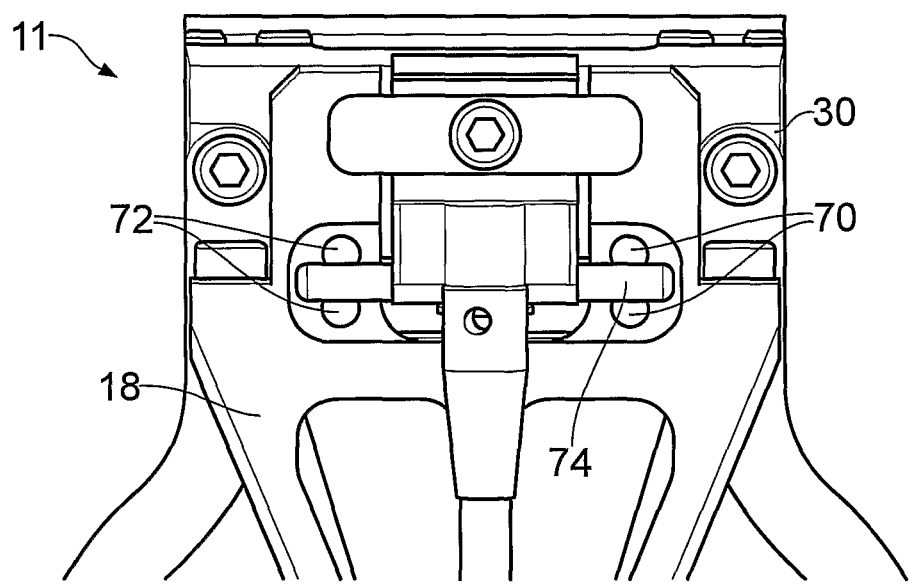
FIGS. 4b and 4c show a detailed view of the sprung end of the indexer frame shown in FIG. 1b.
Figure 4C:
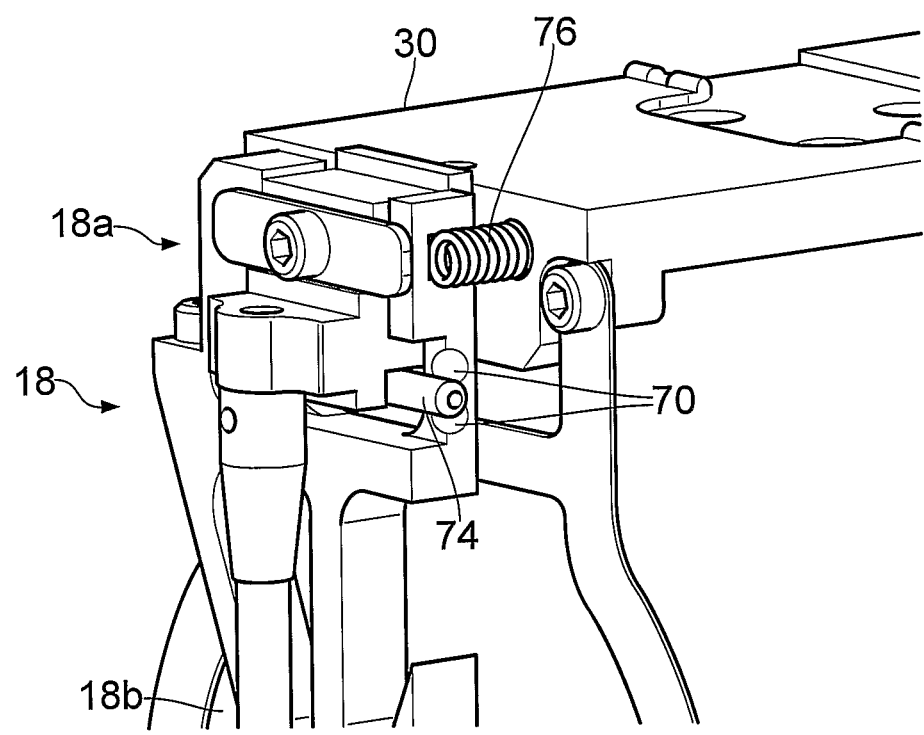

FIGS. 4b and 4c show in more detail the sprung end member 18 of the indexer frame 13 shown in FIG. 1b. Instead of a pair of crossed planar springs 68, as described above, a ball and roller arrangement is used to pivot the sprung end member 18 relative to the indexer frame body 30. A coil spring 76 is positioned between the proximal end 18a of the sprung end member 18 and the indexer frame body 30, biasing the proximal end 18a of the sprung end member 18 away from the indexer frame body 30 and thus biasing the distal end 18b of the sprung end member 18 towards the fixed end member 16 (not shown). Two pairs of adjacent balls 70, 72 are pressed into recesses in the sprung end member 18. The two pairs of balls 70,72 are spaced across the width of the sprung end member 18, the dips between the adjacent balls forming a channel into which a roller 74 is positioned, such that the roller 74 runs through the channel between the adjacent balls of both pairs of balls 70,72. The roller 74 is fixed to the indexer frame 30 by a screw (not shown). As the distal end 18b of the sprung end member 18 is moved away from the fixed end member 16 (by manual force against the bias) the balls 70, 72 slide around the roller, pivoting the sprung end member 18 about the roller 74. The proximal end 18a of the sprung end member 18 is thus moved towards the indexer frame, compressing the spring 76. The distance between the end members is increased in this way in order to position the billet holder in the indexer frame or to remove the billet holder from the indexer frame.

Figure 5:
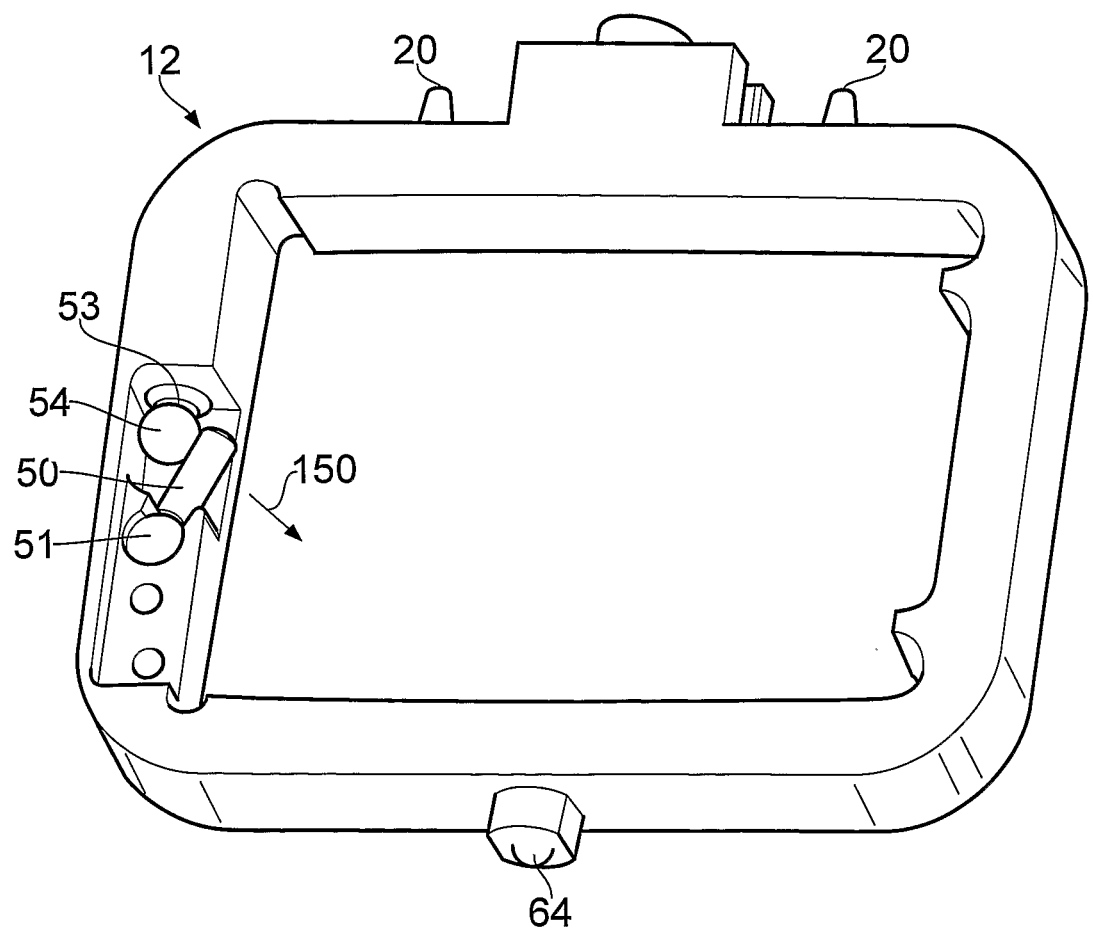
FIG. 5 shows a billet holder for use with an indexer according to the present invention.

FIGS. 4a and 5 show the mechanism used by the billet holder 12 to hold a billet in place. A grub screw 53 runs along a threaded shaft in the wall of the billet holder 12 exiting the shaft into a cavity 56 (also in the wall of the billet holder 12).

The cavity 56 houses a ball 54, situated towards the side of the cavity where the grub screw 53 enters, and a ball ended rod 50, situated with its ball end on the far side of the cavity from the grub screw 53, and its rod end proximal to the ball 54. The ball end of the ball ended rod 50 is secured within the cavity by a part circular recess 51. This arrangement prevents the ball ended rod 50 form falling out of the cavity 56 but allows the ball ended rod 50 to move when certain forces are applied to it. In the cavity 56 the grub screw 53 contacts a ball 54 which in turn contacts the rod end of the ball ended rod 50.

As the grub screw 53 is tightened, the ball 54 is forced further into the cavity 56 in the wall of the billet holder 12. The ball 54 in turn pushes against the rod end of the ball ended rod 50 forcing the rod end out of the cavity 56 in the direction of the arrow 150, towards a billet (not shown). The screw 53 and the ball 54 fix the ball ended rod 50 tight against a billet, securing the billet in the billet holder 12.

In use the indexer frame 10, holding the billet holder 12, is mounted to a machine structure which is moveable relative to the body of a machine. In a preferred embodiment the indexer frame is mounted to a 'Tripod' machine structure on a dental milling machine, thus enabling movement of the indexer in three degrees of freedom (the machine and machine structure are shown in more detail in FIGS. 10 and 11).

Figure 6:
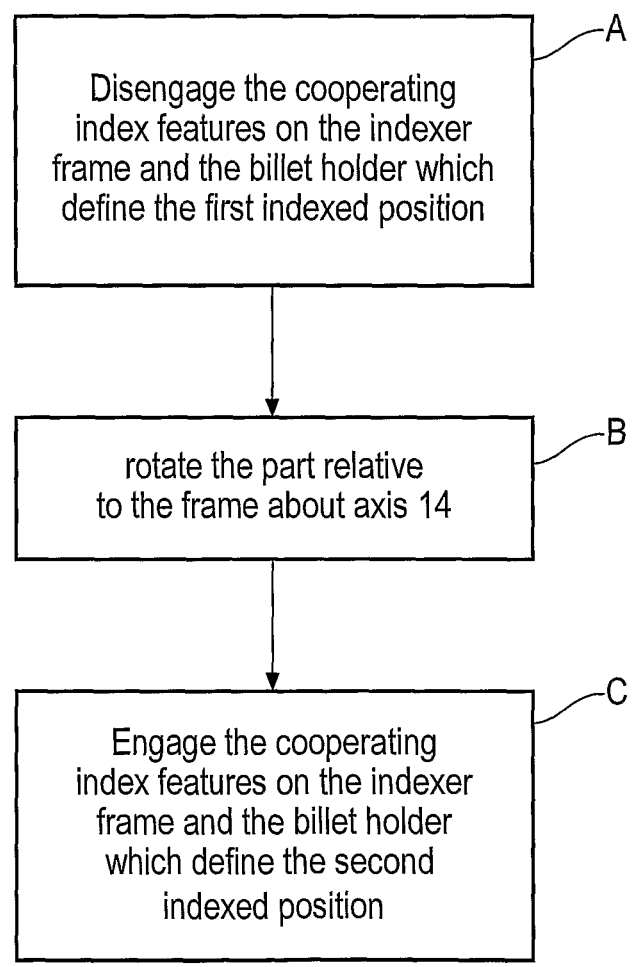
FIG. 6 shows a flow diagram illustrating the steps involved in indexing the billet holder from a first index position to a second index position.

FIG. 6 shows a flow diagram illustrating the steps involved in indexing the billet holder from a first index position to a second index position. The method involves a first step A of disengaging the cooperating index features on the indexer frame and the part which define a first indexed position; a second step B of rotating the part (in this case a billet holder) relative to the frame about an axis; and a third step C of engaging the cooperating index features on the indexer frame and the part which define a second indexed position. The method is described in more detail with reference to FIG. 7 below.

Figure 7:
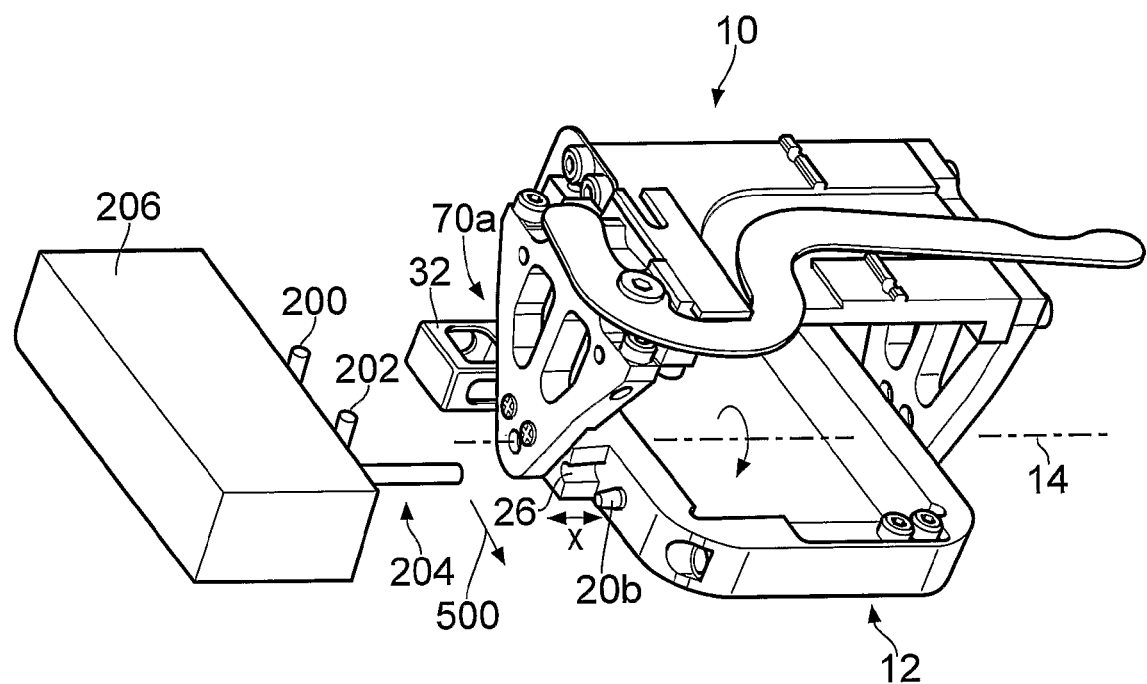
FIG. 7 shows an isometric drawing of an indexer holding a billet holder together with a pin arrangement for rotation of the billet holder with respect to the indexer frame.

FIG. 7 shows an isometric drawing of an indexer holding a billet holder as described with reference to FIG. 1a, together with a pin arrangement for rotation of the billet holder with respect to the indexer frame. The pin arrangement is, in use, fixed to the body of the machine 206 on which the indexer is being used. In order to move the billet holder from its first index position to its second index position a number of steps are carried out. The billet holder 12 is shown in its first indexed position relative to the indexer frame, with the first tapered pin 20a (not shown) engaged in the slot 66 of the locking arm 22.

First the 'Tripod' mechanism of the machine moves the indexer to the body of the machine at the edge of the machine working volume, where three pins (two hook pins 200, 202 and a straight pin 204) are located. The pins are arranged in a straight row, with hook pin 202 lying between hook pin 200 and straight pin 204; the tips of the hooks 200 and 202 lie to one side of the straight row. The machine structure moves the indexer such that hook pin 200 engages into a recessed portion 32 of the locking arm 22. The hook pin 200 holds the arm 22 still relative to the machine body. At this point, the straight pin 204 lies to the side of a groove 26 in the side of the billet holder 12 (described previously with reference to FIG. 1a). The machine structure then moves the indexer frame away from the machine body 206 and the hook pin 200, thus bending the flexible locking arm 22 and disengaging the first tapered pin 20a from the slot 66. In this disengaged position the billet holder 12 is free to rotate relative to the indexer frame about its kinematically located axis 14 (also described with reference to FIG. 1a).

As the tapered pin 20a is disengaged from the slot 66 the machine structure also moves perpendicularly to the axis 14, in the direction of arrow 500 to engage the straight pin 204 into groove 26. At this point, the indexer has been moved away from the machine body such that the locking arm is bent, and the straight pin 204 sits only in the edge of the groove 26. The machine structure then begins to drive the billet holder around the straight pin 204 effecting rotation of the billet holder 12 about its axis 14. Thus, the orientation of the billet holder 12 is changed with respect to the indexer frame 10.

As the structure moves the indexer around the straight pin the first tapered pin 20a is moved so that it is clear of the slot 66. At this point the machine structure moves the indexer back towards the hook pin 200 so that when the recessed portion 32 of the locking arm 22 disengages the first hook pin 200, due to rotation of the indexer about the straight pin 204, the locking arm returns to its biased position without springing too much and disturbing the process. As the structure moves the indexer back towards the machine the straight pin 204 further penetrates the depth x of the groove 26.

As the indexer is moved around the straight pin 204 the billet holder 12 approaches the point at which it will have rotated through 180° with respect to the indexer frame. At this point in the rotation the indexer frame moves over the hook pin 202, which engages into the recessed portion 32 of the locking arm 22. Again, the structure moves the indexer away from the hook pin 202, bending the locking arm 22. The indexer is moved back towards the hook pin 202, returning the locking arm 22 to its biased position, when the second tapered pin 20b on the billet holder is aligned to fit into slot 66. The machine structure finally moves the indexer away from the machine body 206 such that the hook pin 202 is disengaged from the recessed portion 32 of the locking arm 22 and the straight pin 204 is disengaged from the groove 26 in the billet holder 12. Further rotation of the billet holder 12 is prevented by the cooperating pin and slot. Accordingly, the second kinematically located index position is achieved with the second tapered pin 20b located in the slot 66 of the locking arm 22.

Where the indexer and billet holder are as described with reference to FIG. 1b the method is almost the same as described above, with the first locking arm 23a and the tapered pin 20 engaged in the first position. There is however a small difference in the final step of engaging the cooperating index features on the indexer frame and the part which define a second indexed position. As the indexer 11 of FIG. 1b has two locking arms 23a,b and the billet holder 13 has only one tapered pin 20, the hook pins 200 and 202 are spaced further apart. The larger spacing between the hook pins is such that after moving the indexer 11 around the straight pin 204, where the billet holder 13 approaches the point at which it will have rotated through 180° with respect to the indexer frame, it is the recessed portion 32 of the second locking arm 23b which moves over and engages the hook pin 202 (rather than the recessed portion of the only locking arm 22 in the description with reference to the indexer of FIG. 1a). Again, the structure moves the indexer 11 away from the hook pin 202, bending the second locking arm 23b away from its biased position. The indexer 11 is moved back towards the hook pin 202, returning the locking arm 23b to its biased position, when the tapered pin 20 on the billet holder is aligned to fit into slot 66 of the second locking arm 23b. The machine structure finally moves the indexer away from the machine body 206 such that the hook pin 202 is disengaged from the recessed portion 32 of the locking arm 22 and the straight pin 204 is disengaged from the groove 26 in the billet holder 13. Further rotation of the billet holder 13 is prevented by the cooperating pin and slot. Accordingly, the second kinematically located index position is achieved with the tapered pin 20 located in the slot of the second locking arm 23b.

Figure 8:
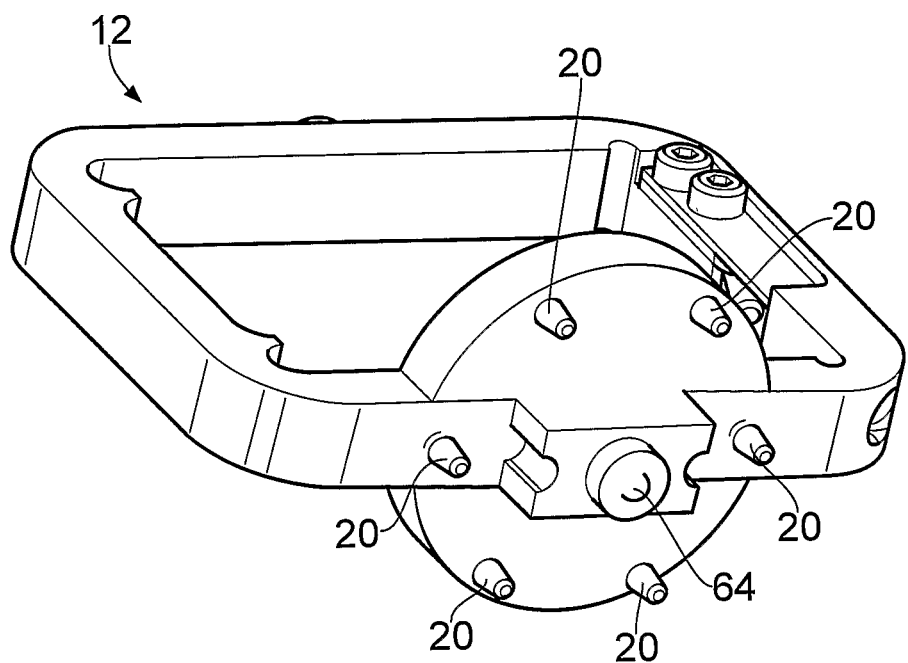
FIG. 8 shows an alternative embodiment of the billet holder 12 which has multiple index positions.

FIG. 8 shows an alternative embodiment of the billet holder 12 which has multiple index positions. The billet holder 12 has six index features 20, allowing six kinematically located positions when used with the indexer frame as previously shown in FIGS. 1a, 1b and 2. The slot 66 of the indexer frame cooperates with one of the reference features 20 to provide a kinematically located index position. The method described with reference to FIGS. 6 and 7 can then be followed to index the part between the index positions.

Figure 9:
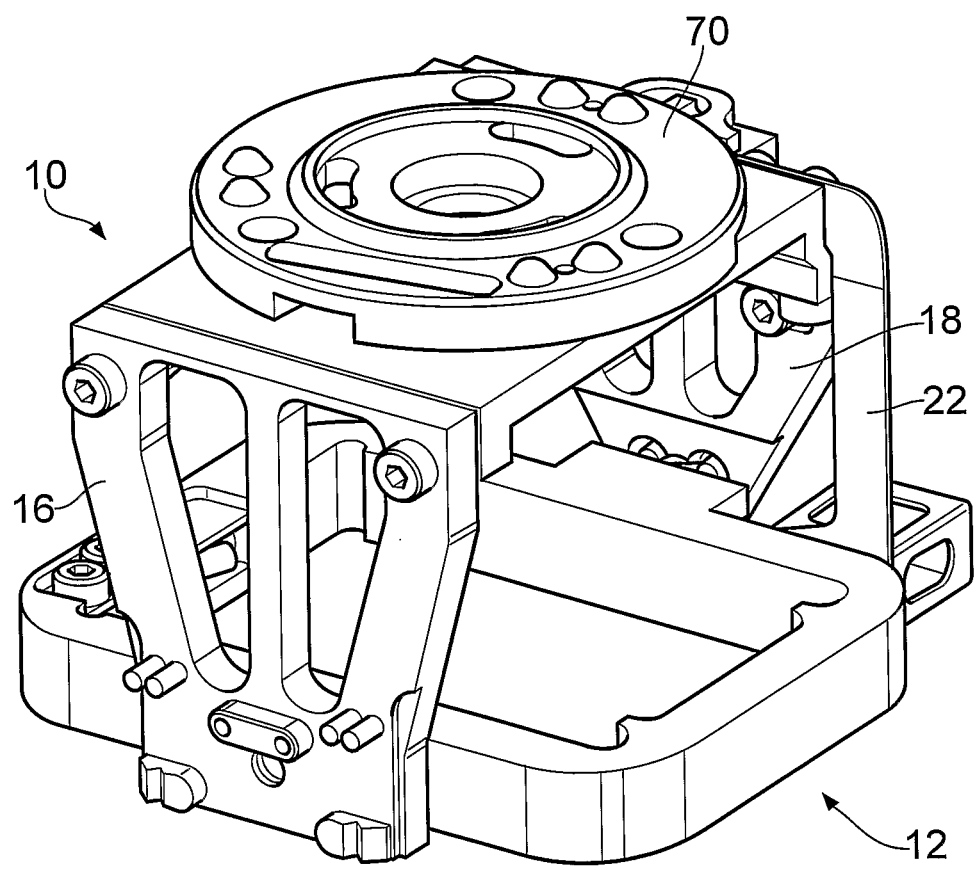
FIG. 9 shows an indexer adapted for mounting to a machine.

FIG. 9 shows the indexer 10 with a mount 70 affixed to the indexer frame body 30, on the opposite side of the indexer frame body 30 to that on which the billet holder is held. The mount 70 allows the indexer to be mounted to the 'Tripod' platform of a Renishaw dental scanning or milling machine. The mount is a kinematic mount as disclosed in the co-pending PCT application filed on the same day as the present application with the title 'Modular Scanning and Machining Apparatus', having the applicant's reference number 0771/WO/0 and claiming priority from UK Patent Application no. 0803667.5. Subject matter that is disclosed in that application is incorporated in the specification of the present application by this reference.

Figure 10:
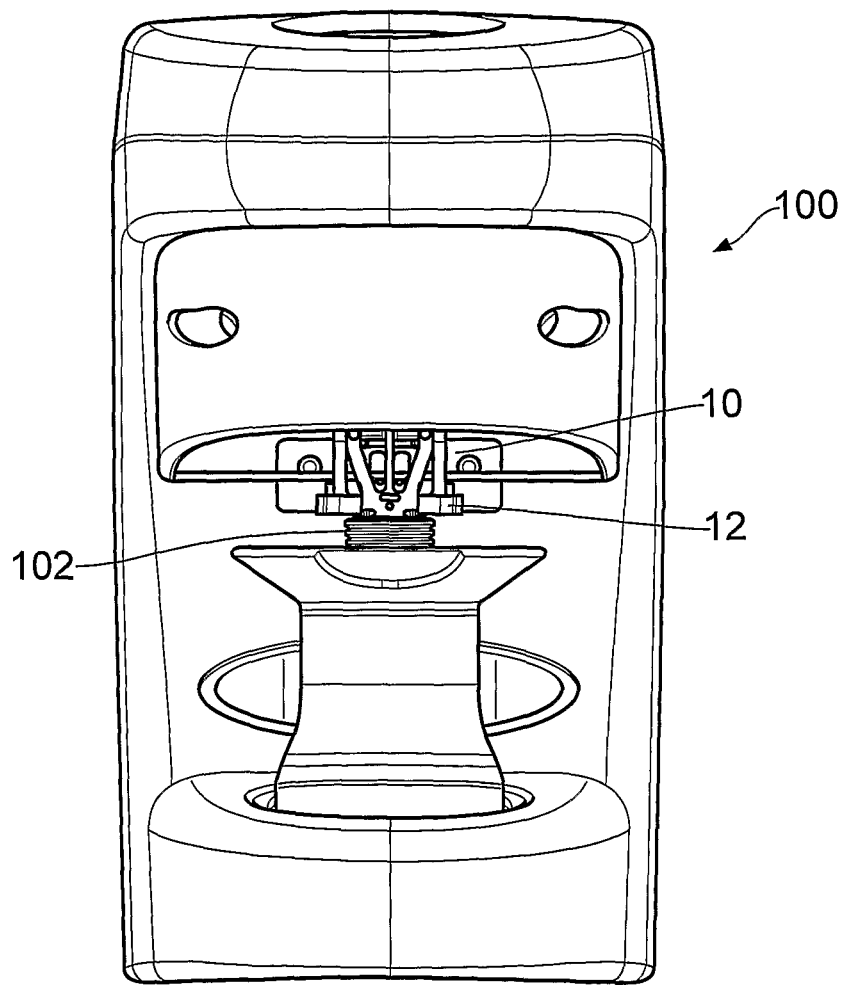
FIG. 10 shows a front view of an example of a dental milling machine with which the indexer of FIG. 1 to 8 may be used.

FIG. 10 shows a front view of an example of the type of machine that the indexer may be mounted to. The machine is a dental milling machine 100. The indexer 10 is mounted on the 'Tripod' platform (concealed by the machine outer case) such that the billet and billet holder 12 are suspended over an upwards pointing milling tool (concealed by bellows 102). Although a dental milling machine of this type is shown, the indexer may be mounted to any other type of machine.

Figure 11:
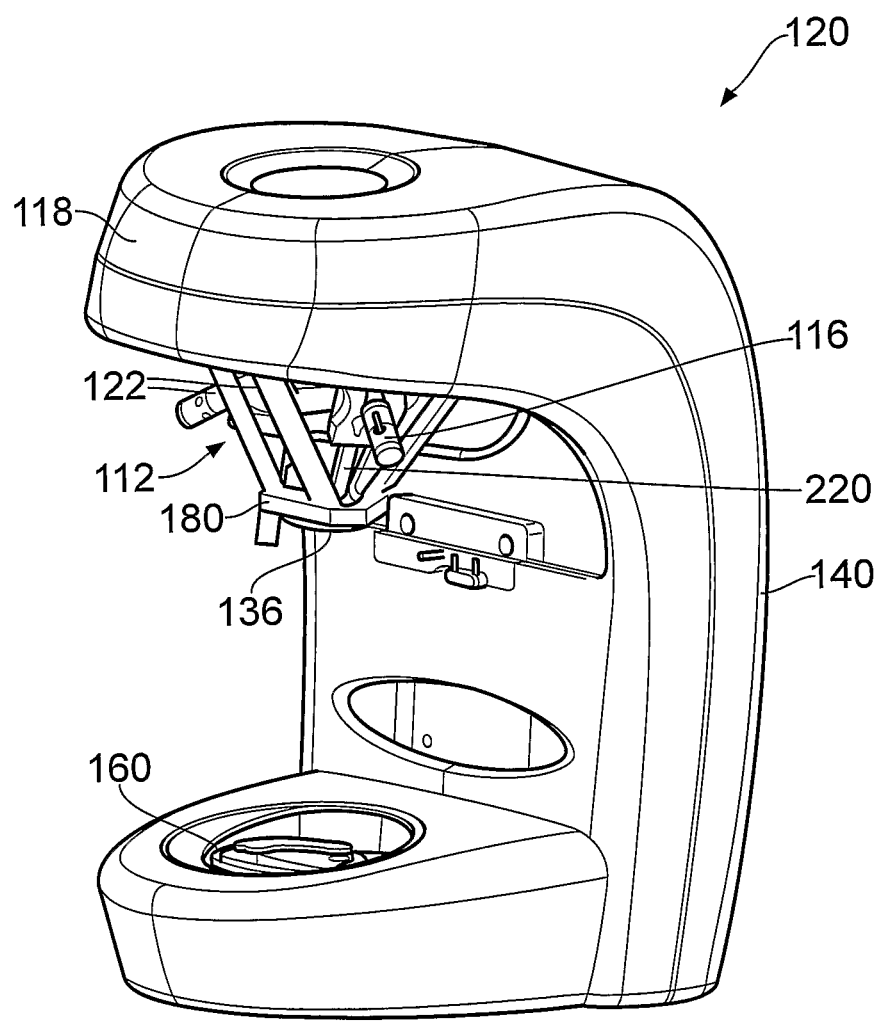
FIG. 11 shows an isometric view of a machine structure to which an indexer according to the present invention may be mounted.

FIG. 11 shows the 'Tripod' machine structure, to which the indexer may be mounted, in more detail. The machine structure 120 generally comprises a body 140 having a fixed base 160 and a fixed head 118, mounted to which is a platform 180 that is generally opposite to and facing the fixed base 160.

The platform 180 is coupled to the head 118 of the body 140 via three telescopic struts 220, each strut being connected to the platform 180 and the head 118 of the body at its respective upper and lower ends by spherical joints. Each strut 220 has a motor 116 to increase or decrease its length. Each motor 116 comprises a tachometer for measuring the rotational speed of the drive shaft in the motor. Furthermore, a scale and a readhead for reading the scale (not shown) are provided on the back of each strut 220. The outputs of the tachometers and readheads are provided to a computer for use in a feedback loop to enable accurate control of the movement of the platform as described in more detail below.

As the platform 180 is supported only by the three telescopic struts 220 which are connected to the upper and lower stages by spherical joints, this platform may rotate about three perpendicular axes relative to the head 118. To prevent this, three anti-rotational devices 112, comprising a pair of struts 122 and a rotation restrictor (not shown), are provided which eliminate these three degrees of rotational freedom whilst allowing translational movement. The devices are passive, i.e. they have no motor or other actuator. The joints between the anti-rotational devices 112 and the platform 180 and the head 118 are also pivot joints. Accordingly, the struts 220 and anti-rotational devices 112 facilitate movement of the platform 180 relative to the body 140 in three mutually perpendicular dimensions (i.e. x, y and z dimensions), under the control of a computer. Such an arrangement for providing linear-only relative movement of a platform 180 relative to a fixed head 118 is known, and described for example in EP 0674969 and U.S. Pat. No. 7,241,070, the entire contents of which are incorporated by these references. As will be understood, mechanisms other than the one described above can be used for facilitating relative movement between the platform 180 and the head 118. In particular, it need not be necessary to restrict rotation of the platform 180 relative to the head 118.

In use the mount 70 (as shown in FIG. 9) of the indexer is mounted to a kinematic mount formation 136 on the platform 180 such that movement of the 'Tripod' structure controls movement of the indexer.

The invention claimed is:

1. An indexer for providing rotation of a part from a first index position to a second index position comprises:
    an indexer frame and a part for rotation, said indexer frame having at least one index feature, and said part having at least one index feature, wherein the at least one index feature on the indexer frame is co-operable with the at least one index feature on the part so as to provide two or more index positions of the part with respect to the indexer frame;
    wherein in use the part locates with the indexer frame so as to form an axis about which the part is able to rotate relative to the indexer frame, said axis being kinematically located and defined by at least two spaced apart engagement locations between the indexer frame and the part, a first one of the engagement locations providing a constraint in at least one degree of freedom and the least one other engagement location being compliant in at least one of the degrees of freedom that the first engagement location provides constraint.

2. An indexer according to claim 1, in which the at least one other engagement location is compliant in a dimension parallel to the axis.

3. An indexer according to claim 1, in which the first one of the engagement locations is configured to constrain a point of the axis in at least three mutually perpendicular translational degrees of freedom.

4. An indexer according to claim 1, in which the at least one other engagement location is configured to constrain movement of the axis in at least two rotational degrees of freedom.

5. An indexer according to claim 1 wherein the indexer frame comprises two opposing frame ends spaced apart by a frame body.

6. An indexer according to claim 1 wherein one frame end is biased towards the other end frame by a bias mechanism.

7. An indexer according to claim 6 wherein the bias mechanism comprises a spring.

8. An indexer according to claim 1 wherein the said location between the part and the indexer frame is facilitated by cooperation between corresponding recesses and protrusions provided on the part and indexer frame at two locations.

9. An indexer according to claim 8 wherein the recesses comprise triangular recesses.

10. An indexer according to claim 8 wherein the protrusions comprise balls.

11. An indexer according to claim 1 wherein the indexer frame is configured to have a first position for locating the part and a second position beyond which the part is released.

12. An indexer according to claim 11 wherein movement between said first and second position is provided for by the moveable frame end.

13. An indexer according to claim 12 wherein the moveable frame end is sprung with respect to the indexer frame so as to allow movement between said first and second positions.

14. An indexer according to claim 1 wherein the indexer is adapted for mounting on dental apparatus.

15. An indexer according to claim 1 wherein the part comprises a billet holder.

16. An indexer according to claim 1 wherein the part comprises a billet for machining dental parts from.

17. An indexer according to claim 1 wherein two index positions of the part with respect to the indexer frame are provided.

18. An indexer according to claim 1 wherein the index positions are kinematically located.

19. An indexer according to claim 18 wherein the kinematic location of the index positions is achieved by cooperating index features provided on the part and the indexer frame.

20. An indexer according to claim 1 wherein the index features comprise a protrusion on the part and a recess on the indexer frame.

21. An indexer according to claim 20 wherein the protrusion is a tapered pin.

22. An indexer according to claim 20 wherein the recess is a slot with at least two straight sides.

23. An indexer according to claim 1 wherein the index features comprise a protrusion on the indexer frame and a recess on the part.

24. An indexer according to claim 1 wherein any index features on one of the part and the indexer frame are moveable relative to any index features on the other of the part and the indexer frame between an engaging and a disengaging position.

25. An indexer according to claim 24 wherein the moveable index feature is provided on an arm sprung with respect to the indexer frame.

26. An indexer according to claim 1, in which the part is able to rotate relative to the indexer frame through at least 180°.

27. A part for use with an indexer as claimed in claim 1, said part comprising features for defining at least two spaced apart engagement locations between the indexer frame and the part, a first one of the engagement locations providing a constraint in at least one degree of freedom and the at least one other engagement location being compliant in at least one of the degrees of freedom that the first engagement location provides against constraint.

28. An indexer frame for use with an indexer as claimed in claim 1, said indexer frame comprising features for defining at least two spaced apart engagement locations between the indexer frame and the part, a first one of the engagement locations providing a constraint in at least one degree of freedom and the at least one other engagement location being compliant in at least one of the degrees of freedom that the first engagement location provides constraint.

29. A method for indexing a part located in an indexer frame and rotated about a kinematic axis defined by at least two spaced apart engagement locations between the indexer frame and the part, a first one of the engagement locations providing a constraint in at least one degree of freedom and the at least one other engagement location being compliant in at least one of the degrees of freedom that the first engagement location provides constraint, between a first index position relative to the indexer frame and a second index position relative to the indexer frame, comprises:
- disengaging a first set of cooperating index features on the indexer frame and the part, said index features defining a first index position of the part relative to the frame;
- rotating the part relative to the frame about the kinematic axis;
- engaging a second set of cooperating index features on the indexer frame and the part, said index features defining a second index position of the part relative to the frame.

30. A method according to claim 29, in which the at least one other engagement location is compliant in a dimensional parallel to the axis.

31. A method according to claim 29, in which the first one of the engagement locations is configured to constrain a point of the axis in at least three mutually perpendicular translational degrees of freedom.

32. A method according to claim 29, in which the at least one other engagement location is configured to constrain movement of the axis in at least two rotational degrees of freedom.

33. A method according to claim 29 wherein the index feature on one of the part and the frame is the same index feature for the first and second sets of cooperating index features.

34. A method according to claim 29 wherein the first set of cooperating index features comprises a first index feature on the indexer frame and a first index feature on the part; and the second set of cooperating index features comprises the first index feature on the indexer frame and a second index feature on the part.

35. A method according to claim 29 wherein the index features comprise a tapered pin and a slot.

36. A method according to claim 29 wherein an index feature on the indexer frame is provided on an arm sprung with respect to an indexer frame body.

37. A method according to claim 29 wherein the index feature provided on the arm is disengaged from any index features on the part by movement of the arm away from its biased position.

38. A method according to claim 37 wherein the arm is moved away from its biased position by interaction with a feature on the machine body.

39. A method according to claim 29, comprising rotating the part relative to the frame about the kinematic axis through at least 180°.

40. An indexer for providing rotation of a part from a first index position to a second index position comprises:
- an indexer frame and a part for rotation, said indexer frame having at least one index feature, and said part having at least one index feature, wherein the at least one index feature on the indexer frame is co-operable with the at least one index feature on the part so as to provide two or more index positions of the part with respect to the indexer frame;
- wherein in use the part locates with the indexer frame so as to form an axis about which the part is able to rotate relative to the indexer frame, said axis being kinematically located and defined by at least two spaced apart engagement location between the indexer frame and the part, at least one of which provides compliance in at least one degree of freedom that the at least one other one provides constraint.

41. An indexer for providing rotation of a part from a first index position to a second index position comprises:
- an indexer frame and a part for rotation, said indexer frame having at least one index feature, and said part having at least one index feature, wherein the at least one index feature on the indexer frame is co-operable with the at least one index feature on the part so as to provide two or more index positions of the part with respect to the indexer frame;
- wherein in use the part locates with the indexer frame so as to form an axis about which the part is able to rotate relative to the indexer frame, said axis being kinematically located and defined by at least two spaced apart engagement locations comprising cooperating features on the part and indexer frame, said cooperating features of a first one of the engagement locations being configured to constrain the axis in at least three mutually perpendicular translational degrees of freedom, and the cooperating features of the at least one other engagement location being configured to constrain the axis in at least two rotational degrees of freedom, in which the at least one other engagement location is compliant in a dimension parallel to the axis.

42. An indexer for providing rotation of a part from a first index position to a second index position comprises:
- an indexer frame and a part for rotation, said indexer frame having at least one index feature, and said part having at least one index feature, wherein the at least one index feature on the indexer frame is co-operable with the at least one index feature on the part so as to provide two or more index positions of the part with respect to the indexer frame rotationally;
- wherein in use the part locates with the indexer frame so as to form an axis about which the part is able to rotate relative to the indexer frame through at least 180°, said axis being kinematically located.

43. A method for indexing a part located in an indexer frame and rotated about a kinematic axis between a first index position relative to the indexer frame and a second index position relative to the indexer frame, comprises:
- disengaging a first set of cooperating index features on the indexer frame and the part, said index features defining a first index position of the part relative to the frame;
- rotating the part relative to the frame about the kinematic axis through at least 180°;
- engaging a second set of cooperating index features on the indexer frame and the part, said index features defining a second index position of the part relative to the frame.

* * * * *